US005453084A

United States Patent [19]
Moses

[11] Patent Number: 5,453,084
[45] Date of Patent: Sep. 26, 1995

[54] VASCULAR GRAFT WITH INTERNAL SHUNT

[76] Inventor: John A. Moses, 80 Laslo Ter., Fairfield, Conn. 06430

[21] Appl. No.: 63,867

[22] Filed: May 19, 1993

[51] Int. Cl.⁶ .............................. A61M 5/00; A61F 2/04
[52] U.S. Cl. .................................. 604/8; 623/12
[58] Field of Search ........................ 604/8, 9, 174, 604/175, 4, 5, 6; 623/1, 11, 12; 606/153, 194; 600/36

[56] References Cited

U.S. PATENT DOCUMENTS

| 3,435,824 | 4/1969 | Gamponia | 604/8 |
| 3,516,408 | 9/1969 | Montanti | 604/8 |
| 3,826,257 | 7/1974 | Buselmeier | 604/8 |
| 3,853,126 | 12/1974 | Schulte | 604/8 |
| 4,192,302 | 3/1980 | Boddie | 128/214 |
| 4,574,000 | 3/1986 | Hunter | 604/8 |
| 4,639,252 | 1/1987 | Kelly et al. | 604/282 |
| 4,712,551 | 12/1987 | Rayhanabad | 128/334 |
| 4,950,226 | 8/1990 | Barron | 604/8 |
| 4,979,937 | 12/1990 | Knorasani | 604/8 |
| 5,021,045 | 6/1991 | Buckberg et al. | 604/53 |
| 5,135,474 | 8/1992 | Swan et al. | 604/8 |
| 5,267,940 | 12/1993 | Moulder | 604/8 |

FOREIGN PATENT DOCUMENTS 0216691  4/1987  European Pat. Off. .................. 604/8

Primary Examiner—Debra S. Brittingham
Attorney, Agent, or Firm—Charles Blaich

[57] ABSTRACT

A vascular graft which incorporates a flexible shunt to significantly reduce the time that blood flow to vital organs and extremities is interrupted during removal of diseased sections of a blood vessel.

6 Claims, 4 Drawing Sheets

VASCULAR GRAFT WITH INTERNAL SHUNT

BACKGROUND OF THE INVENTION

Aortic surgery that is required to replace diseased portions of the thoracic and abdominal aorta appears to be increasing. In the past, resection of the thoracic aorta and replacement of the resected section with a graft was performed as an emergency operation to repair a ruptured vessel due to gun or knife wounds or auto accidents and the like. With the advent of the newer non-invasive examining equipment and techniques such as CT and MRI it appears that aneurysms of the thoracic aorta and abdomen occur fairly often with the patient not being aware of the problem other than a "back problem" or shooting pains in the legs. Such aneurysms may occur anywhere along the thoracic or abdominal aorta from the arch of the aorta to its bifurcation into the femoral arteries. Most commonly it appears that such aneurysms occur at the bifurcation point and extend upward into the abdominal aorta.

Most of the aneurysms are caused by arteriosclerotic action on the walls of the aorta resulting in loss of elasticity and weakening of the aortal walls resulting in ballooning or localized dilation of the aorta. When such dilation approaches or exceeds a diameter of 6 cm. rupture of the aorta is imminent.

In addition to aneurysms, occlusion or partial blockage of the aorta may occur. Such occlusion is usually caused by progressive degenerative changes in the wall of the blood vessel.

Physiologically both conditions result in loss of blood supply to the lower part of the body which if below the renal arteries can result in gangrene of the lower extremities. If above the renal arteries, loss of kidney function may occur because of the reduction of blood supply to the kidneys.

A common surgical repair technique that is currently used is to clamp the abdominal aorta above the aneurysm or occlusion and at the femoral arteries shutting down blood flow to the lower extremities and abdominal organs and lower spinal cord. If the aneurysm/occlusion is in the renal, lumbar and mesenteric arteries area of the abdomen, clamping of the aorta can be done in the exposed abdomen. However, if the lesion extends into the thoracic cavity one side of the thoracic cavity must be exposed and the thoracic aorta proximally clamped above the diaphragm. Even with modern surgical techniques the length of time such shut down extends is usually longer than one hour. During this time metabolism of the now stagnated blood continues resulting in ischemia and production of plasma purines, lactic acid and several other toxic metabolites which have deleterious vasoactivity. Further, the effect of clamping severely increases blood pressure above the clamp resulting in substantial strain on the heart.

When a graft has been inserted and blood vessels connected, the clamps are removed allowing instantaneous return of blood flow. This most often results in dangerous hypotension, blood acidosis and kidney vasoconstriction. Appropriate pharmacology, if rendered quickly, can manage the hypotension and acidosis but the restriction of blood flow through the kidneys and their hemodynamic phenomena can be serious and life threatening.

Through the years numerous external shunts of the prior art have been developed to act to transport arterial blood around the closed off section of the aorta to be connected to the organ and femoral arteries to prevent such problems. Such shunts require additional surgery for example to expose and insert a shunt into the subclavian arteries and subsequently into the femoral and organ arteries. Much data has been collected to identify the value of such shunts as has data refuting the same because of problems caused by additional surgery and time required therein.

PRIOR ART

A preliminary search for patentability uncovered the following art:

| U.S. Pat. No. | Inventor | Title |
|---|---|---|
| 5,135,474 | Swan et al. | HEPATIC BYPASS CATHETER |
| 5,021,041 | Buckberg et al. | RETROGRADE VENOUS CARDIOPLEGIA CATHETERS METHODS OF USE AND MANUFACTURE |
| 4,979,937 | Khorasani | METHOD AND APPARATUS INVOLVING INTERCOSTAL AND LUMBAR PROFUSION |
| 4,950,226 | Barron | SURGICAL SHUNT FOR LIVER ISOLATION |
| 4,712,551 | Rayhanabad | VASCULAR SHUNT |
| 4,639,252 | Kelly et al. | VENOUS RETURN CATHETER |
| 4,192,302 | Boddie | HEPATIC ISOLATION AND PERFUSION CIRCUIT ASSEMBLY |

Swan et al. issued Aug. 4, 1992, teaches a bypass catheter to occlude liver blood flow resulting in zero blood pressure in the liver for surgery.

Buckberg et al. issued Jun. 4, 1991, teaches catheters designed for rapid and accurate insertion into the coronary sinus for retrograde administration of cardioplegia.

Khorasani issued Dec. 25, 1990, teaches an internal aortal shunt with a plurality of side members for providing blood flow to distal members and intercostal (lumbar) arteries.

Barron issued Aug. 21, 1990, teaches a shunt to isolate liver and its veins from normal blood reperfusion during liver surgery.

Rayhanabad issued Dec. 15, 1987, teaches an external aortal shunt for insertion into the aorta above the resection area which has a sealing cuff to block flow of blood and a number of tubular branches to be connected to arteries serving various organs of the body.

Kelly et al. issued Jan. 27, 1981, teaches a venous return catheter for drawing blood from the right atrium and vena cava for treatment in extracorpal life support equipment.

Boddie issued Mar. 11, 1980 teaches a venous shunt to isolate blood flow to and through the liver for chemotherapy of the same.

None of the prior art herein described is thought to reflect on the instant invention which is a device to incorporate arterial shunts into a preformed aortal graft which results in significantly shorter time to perform aortal resection and insertion of the graft.

BRIEF DESCRIPTION

In its simplest form (FIG. 2) clear, flexible tubing larger than 9 mm. internal diameter is incorporated into a cylindrical graft which is sized to conform to the diameter of the aorta. Rather than directly passing through the graft, the tubing exits through a sleeve (proximal) extends around a loop and back through a second sleeve (distal), thence through the remaining graft. The tubing is of sufficient length to extend well beyond the open proximal and distal ends of the graft. The loop permits visual monitoring of blood flow and an area which in turn may be clamped to shut down blood flow. The procedure to utilize the shunt and surrounding graft starts by placing vascular clamps on the aorta wall above (proximal) and below (distal) the lesion to temporarily shut down blood supply. The aorta is incised above and below the lesion and the diseased section removed. Air is removed or displaced from the shunt and it is inserted proximally and distally into the aorta and ring clamps or purse string sutures are applied to the outer wall of the aorta to effect a water seal of the aorta inner wall to the shunt at both the proximal and distal ends. Both vascular clamps on the aorta are released to establish circulation through the shunt. Once blood supply has been established the graft surrounding the shunt at the proximal and distal ends is cut to size and sutured to the aorta. Ring clamps or purse string sutures are applied to both the proximal and distal sleeves of the graft to effect a water seal of the graft to the shunt. The proximal and distal ring clamps on the aorta are released to reestablish circulation through the implaced graft. The aorta-graft sutures are inspected to assure that there are no leaks. Assuming none the ring clamps on the proximal and distal sleeves and the shunt are withdrawn through the open sleeves which are then sutured.

BRIEF DESCRIPTION OF THE DRAWINGS

FIG. 4 is a cutaway view of a shunt/graft which extends to and into femoral arteries and has outlets which may extend into other major arteries or be used for sampling, monitoring and the like.

DETAILED DESCRIPTION

In all cases described hereinafter it shall be understood that the graft material is woven fabric such as polyester or polytetrafluoroethylene fabric which is in common usage for vascular surgery. The tubing used for the shunt is formed from elastic materials which are flexible and have flexural moduli such that they will not crimp or occlude when bent 90° or so. Further, the materials must be transparent, capable of being heparin coated to prevent blood clotting or attaching to the surface. The family of polymers which meet the above criteria are elastoplastics, such as—polyester and polyether polyurethanes, aliphatic polyesters, modified polyvinyl chlorides, aliphatic polyamides, polyetheramide block polymers, silicon polyamides, styrenebutadiene block polymers.

Figure 1:
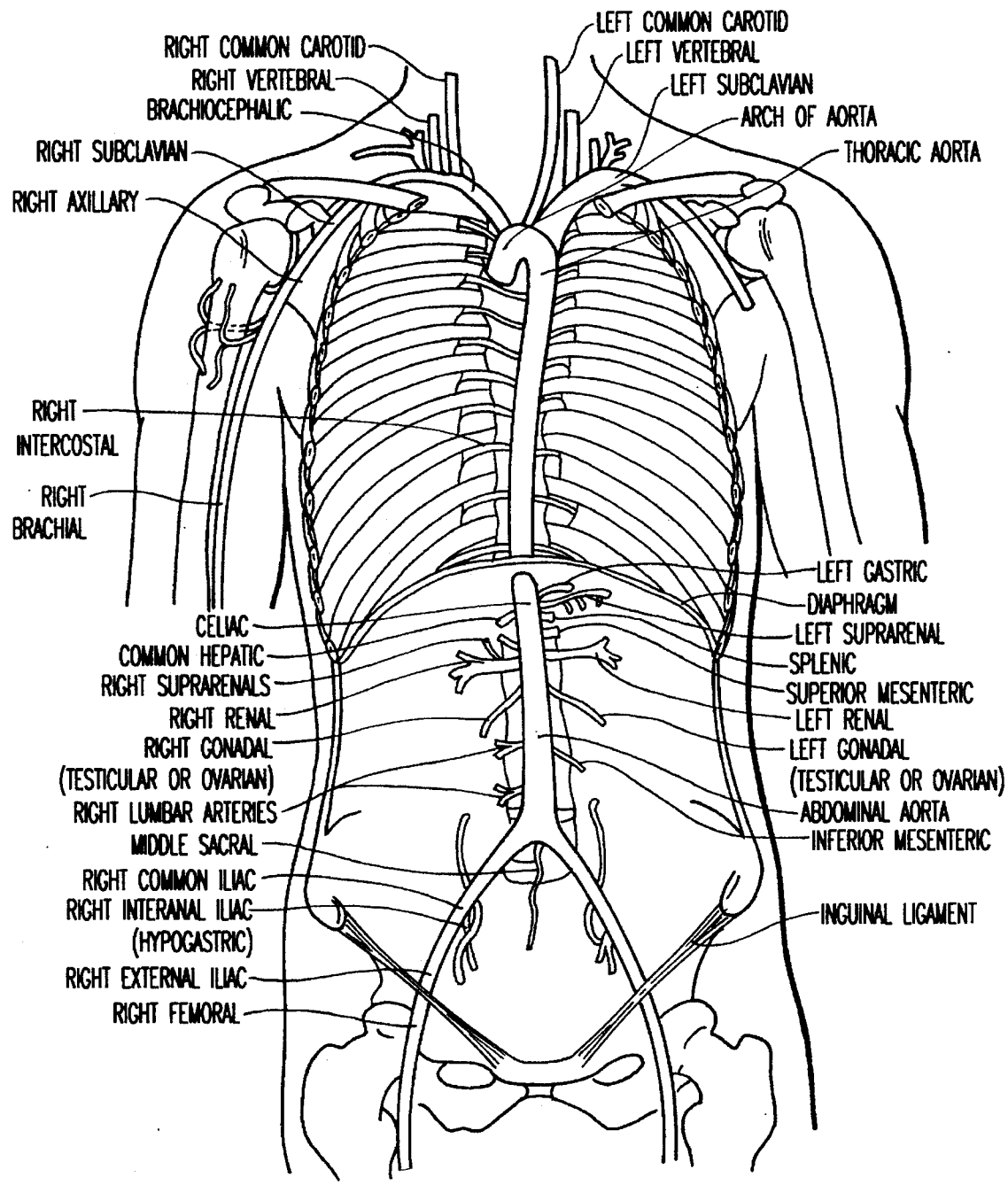
FIG. 1 illustrates the thoracic and abdominal aorta branches in anterior view for reference purposes. (*Principles of Human Anatomy*, Tortora, Gerard J. Harper & Row, p.326).

FIG. 1 is included herein to act as a reference for the functions described herein.

Figure 2:
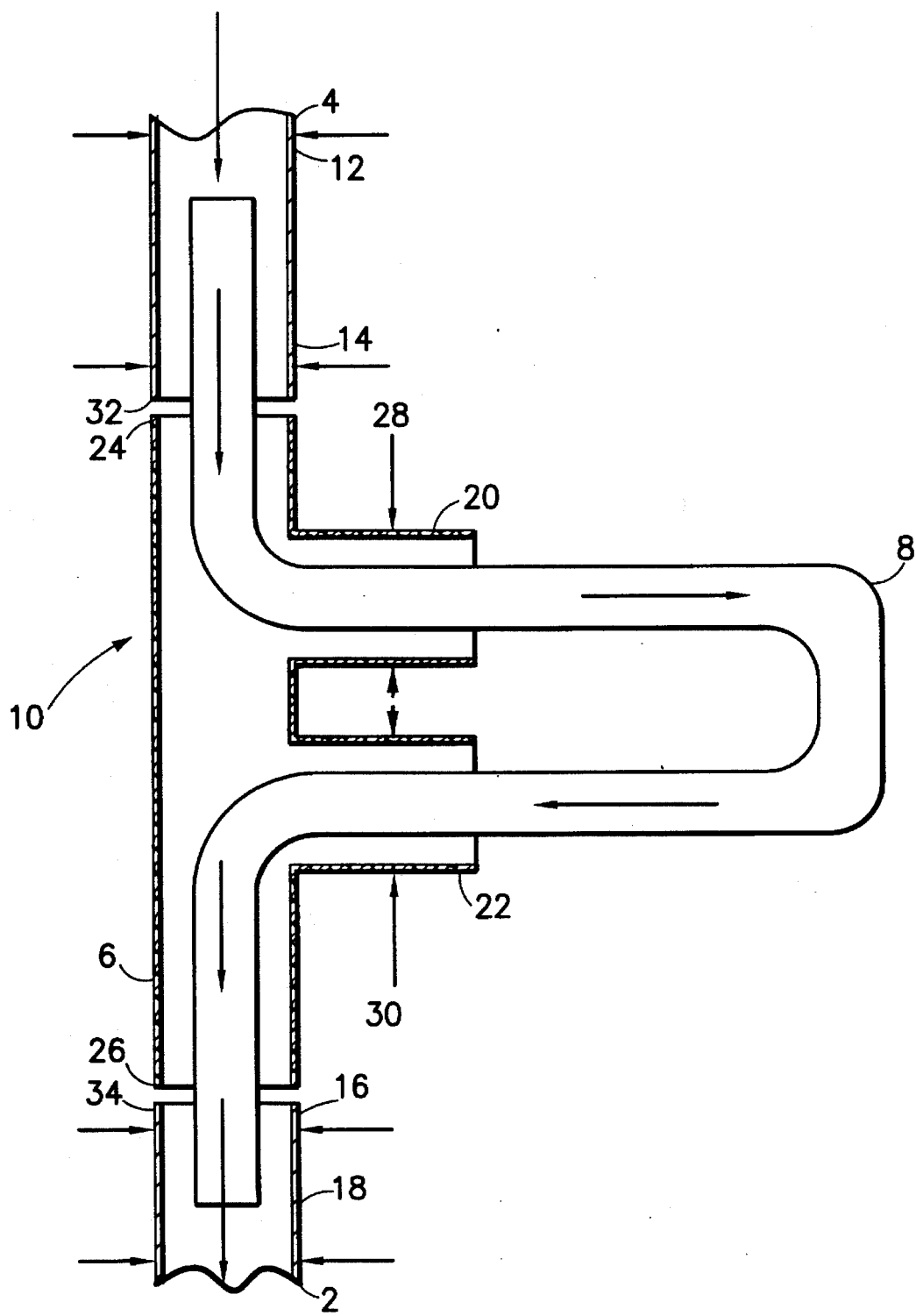
FIG. 2 is a cutaway view of the basic shunt graft and aorta of this invention.

In a first simple aortic graft with internal shunt 10 FIG. 2 shown in cross section in place in the resected aorta. Flexible transparent tube 8 is incorporated into graft 6 extending beyond both the proximal and distal ends of the graft 24 and 26. Proximal remaining aorta 4 and distal remaining aorta 6 have shunt tube 8 inserted therein well above and below mating graft ends 24 and 26. Vascular clamps have been placed proximally at 12 and distally at 18. Once in place ring clamps are placed at 14 and 16 to effect a water seal between aorta outer wall and shunt outer wall. Ring clamps are also placed on proximal and distal sleeves 20 and 22 at 28 and 30 to effect a water seal between graft sleeve and shunt. Vascular clamps at 12 and 18 are released allowing circulation to be restored through shunt 8 as shown by arrows. Graft ends 24 and 26 are sutured to remaining aorta at 32 and 34. When suturing is complete ring clamps at 14 and 16 are released permitting blood to flow both through the sutured graft and shunt. Assuming no leaks, ring clamps at 28 on proximal sleeve 20 and 30 on distal sleeve 22 are removed and shunt 8 is removed from graft 10 immediately suturing sleeves 20 and 22.

Figure 3:
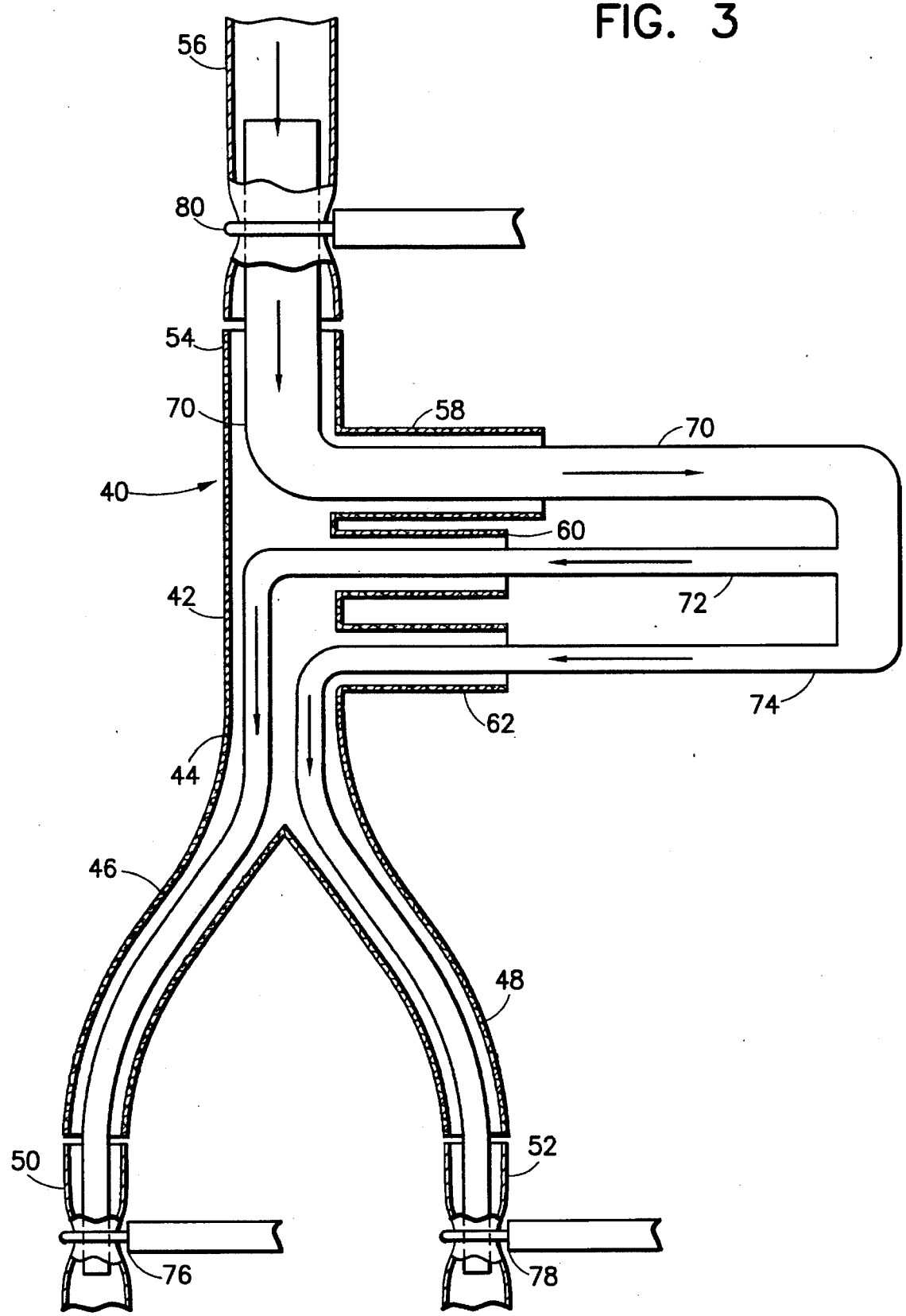
FIG. 3 is a cutaway view of a shunt and graft which splits so as to extend into the femoral arteries.

In a second version FIG. 3, in 40 which both graft and shunt are bifurcated so as to be useful for aorto-femoral artery repair graft 42 bifurcates at 44. Left section 46 and right section 48 being of such length to mate with resected femoral arteries 50 and 52. At the proximal end only one tubular graft 54 is supplied to be attached to aorta 56. Graft 42 has three sleeves 58, 60 and 62. Shunt tube 70 eminates through sleeve 58 and bifurcates into two sections 72 and 74 which extend to and through graft sections 46 and 48 through sleeves 60 and 62 thence to be inserted into femoral arteries 50 and 52. Then water seal effected to the femoral arteries with ring clamps 76 and 78.

Proximal end of shunt 70 is inserted into proximal remaining aorta and ring clamp 80 effects a water seal. Similarly sleeves 58, 60 and 62 are sealed to shunt 70 and shunt sections 72 and 74. As in the previous example vascular clamps on aorta 56 is opened permitting blood to flow through the shunt which suturing of the graft to the aorta and femoral arteries is accomplished. Once suturing is complete clamps on sleeves 58, 60 and 62 are removed and shunt 70 is withdrawn and sleeves are sutured.

Figure 4:
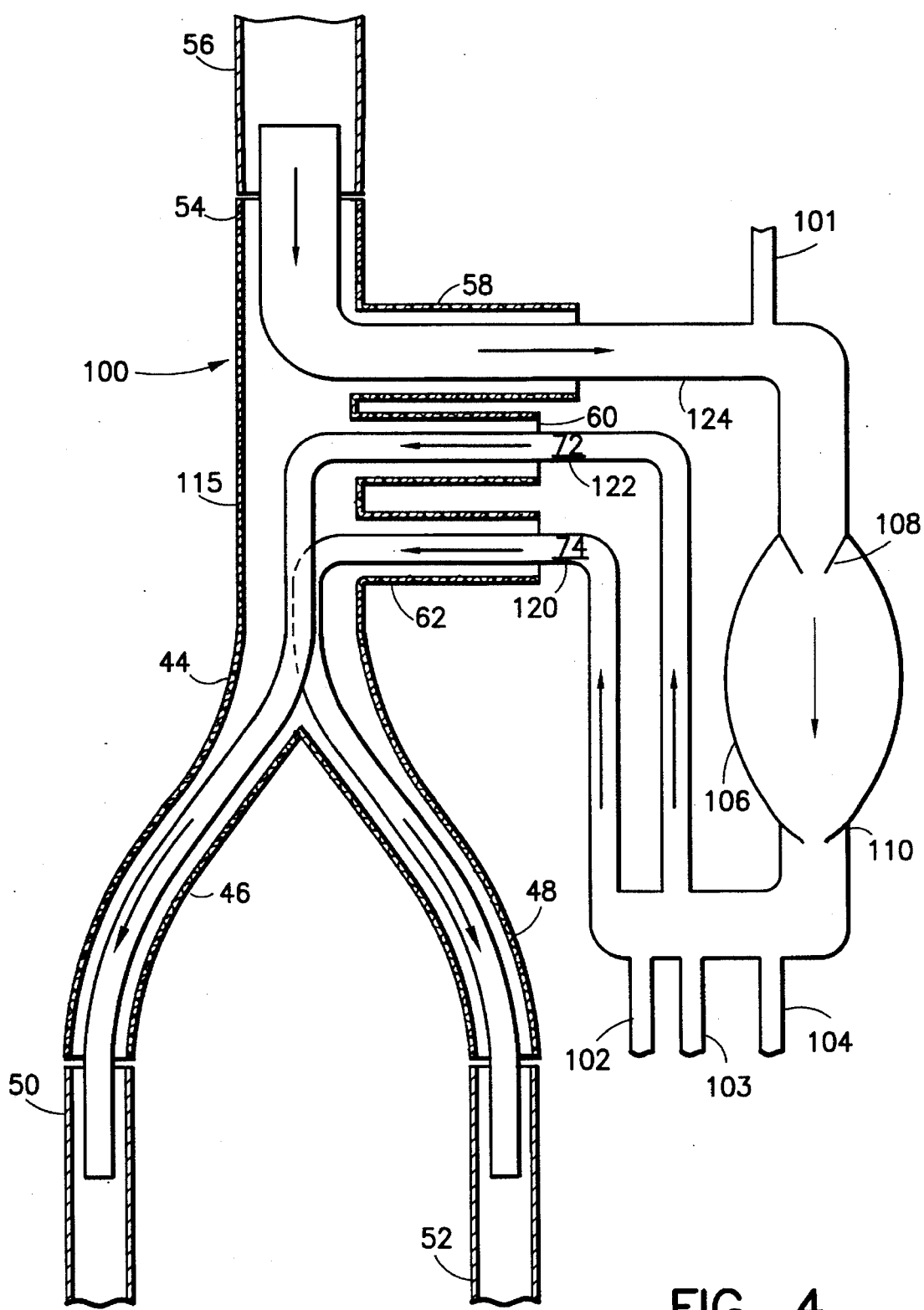

FIG. 4 illustrates a more complex shunt in which several outlets 101, 102, 103 and 104 are supplied in the shunt 100 exterior to graft 115 for perfusion of the kidneys, lumbar arteries and the like as well as to sample blood or otherwise monitor blood flow. In addition, an expansion bulb 106 is provided which has incorporated therein two sets of flapper valves 108, 110 which prevent regurgitation of blood or alternatively may be used as a pump to assist delivery of blood to the lower organs and extremities as in the shunt within a graft illustrated in FIG. 3 the shunt and graft bifurcates to be respectively inserted and sutured into and onto femoral arteries. The surgical procedure for insertion has been previously described differing only in the insertion and ring clamping of outlets 102, 103, 104 into respective organ arteries.

Although the shunts heretofore shown are shown as single continuous tubes it is to be understood that the shunts may be multisectioned with well known water tight fittings being supplied to the sections for easy connection and disconnection and ease of manipulation of the shunt within a graft. For example, complex shunt FIG. 4 could have water tight connections at 120,122 and 124. Thus main proximal aortic shunt 70 femoral shunts 72 and 74 could be connected after insertion into aorta 56 and femoral arteries 50 and 52.

As is well known in the art there are a number of ways to insure effective water seal of a shunt tube to blood vessels. For example an inflatable cuff surrounding the shunt tube may be employed. In such instance the shunt tube and collapsed cuff is inserted into a blood vessel. When implaced the cuff is inflated pressing against the blood vessel's inner wall. Depending upon the integrity and elasticity of the blood vessel's walls it may be used to augument the seal affected by a ring clamp or be used by itself. Alternatively a ridge on the shunt tube's outer wall also may be useful to insure a tight seal of a blood vessle's inner wall.

It will be appreciated that the invention well attains the stated objects and advantages among others.

The disclosed details are exemplary and are not to be taken as limitations on the invention except as those details are included in the appended claims.

What is claimed is:

1. A vascular graft with internal shunt comprising a hollow cylindrical outer member and a semiflexible transparent tubular inner member; said outer member having two open ends, a first open end for suturing proximally to a resected blood vessel, a second open end for suturing distally to said resected blood vessel, said outer member having two woven sleeves extending from one side, a first of said two sleeves being located proximally and a second of said two sleeves being located distally in relationship to said outer member, said inner member being placed within said outer member by threading said inner member through the first open end and through said first sleeve exiting out of said member, returning through one of said sleeves exiting said outer member returning into said outer member through said second sleeve, and said outer member exiting from said second open end, said inner member being internal to said outer member extending from both open ends, said inner member being placed into the resected blood vessel(s) to transport blood while said outer member is sutured in place.

2. A vascular graft according to claim 1 wherein said inner member is an elastoplastic selected from the group consisting of polyether and polyester polyurethanes, aliphatic polyamides, modified polyvinyl chlorides, aliphatic polyamides, polyetheramide block polymers, silicon polyamides, styrene and butadiene block polymers.

3. A vascular graft according to claim 2 wherein said elastoplastic inner member is capable of being coated with heparin to provide a non-blood clotting interior surface.

4. A vascular graft with internal shunt according to claim 2 comprising a hollow cylindrical outer member, and a semiflexible tubular inner member; said outer member having three open ends, a first open end for suturing, proximally to a resected blood vessel, said outer member bifurcated to form two open ends, said two open ends for suturing to two distally resected blood vessels, said outer member having three open sleeves extending from one side, one of said sleeves being proximally located and two sleeves being distally located, said internal shunt member being bifurcated to form three open ends, the first of said three open ends being threaded through said proximally located outer sleeve, to extend beyond said outer members proximal end; the second of said open end of said internal member being threaded through said second outer sleeve to extend beyond said second outer sleeve, said third internal member being threaded through said second outer sleeve to extend beyond said third sleeve, said first inner member being inserted into said proximal end of said resected blood vessel, said second and third inner members being inserted into said distally resected blood vessels, said outer proximal and distal outer sleeves being sutured to said proximal and distal blood vessels while said internal members transport blood until said outer members are sutured in place, said inner members transporting blood until said outer members are sutured in place.

5. A vascular graft according to claim 4 wherein said bifurcated inner members are perforated to supply outlets, said outlets being useful for perfusion of essential organs, sampling of blood and the like.

6. A vascular graft according to claim 4 an expansion bulb is incorporated into one of said bifurcated inner members, said bulb having two flapper valves incorporated therein, the first of said flapper valve bulb being located at the inlet of said bulb, the second flapper valve being located at the outlet of said bulb, said bulb and said internal flapper valves acting in consort when said bulb is squeezed to pump blood into said distal blood vessels.

* * * * *